USO10987127B2

(12) United States Patent
Wilson (10) Patent No.: US 10,987,127 B2
(45) Date of Patent: Apr. 27, 2021

(54) TRANSECTION DEVICE

(71) Applicant: Rutgers, The State University of New Jersey, New Brunswick, NJ (US)

(72) Inventor: Dorian J. Wilson, Bridgewater, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 565 days.

(21) Appl. No.: 15/522,339

(22) PCT Filed: Oct. 30, 2015

(86) PCT No.: PCT/US2015/058337
§ 371 (c)(1),
(2) Date: Apr. 27, 2017

(87) PCT Pub. No.: WO2016/070059
PCT Pub. Date: May 6, 2016

(65) Prior Publication Data
US 2017/0333067 A1    Nov. 23, 2017

Related U.S. Application Data

(60) Provisional application No. 62/073,337, filed on Oct. 31, 2014.

(51) Int. Cl.
*A61B 17/3209* (2006.01)
*A61B 17/32* (2006.01)
(Continued)

(52) U.S. Cl.
CPC .. *A61B 17/3209* (2013.01); *A61B 17/320016* (2013.01); *A61B 17/11* (2013.01);
(Continued)

(58) Field of Classification Search
CPC ........ A61B 17/3211; A61B 17/320016; A61B 2017/32113; A61B 2017/320064;
(Continued)

(56) References Cited

U.S. PATENT DOCUMENTS 2,541,063 A    2/1951  Hubbard
3,007,471 A *  11/1961 McClure, Jr. ...... A61B 10/0266
600/567

(Continued)

FOREIGN PATENT DOCUMENTS

WO    199300860 A1    1/1993

*Primary Examiner* — Wade Miles
*Assistant Examiner* — Kankindi Rwego
(74) *Attorney, Agent, or Firm* — Fox Rothschild LLP (57) ABSTRACT

A transection device including a hollow tubular body extending from a proximal end to a distal end. A plurality of stabilizing members extend from the distal end of the tubular body and define a reduced diameter opening into a receiving chamber adjacent the distal end of the tubular body. A blade is positioned within the tubular body and moveable between an initial position within the tubular body to an extended position wherein at least a portion of the blade extends into the receiving chamber. A depressible member extends from the proximal end and is configured to move the blade between the initial position and the extended position. A compression member may be positioned between the plunger member and the blade.

12 Claims, 5 Drawing Sheets

(51) Int. Cl.
*A61B 17/00* (2006.01)
*A61B 17/11* (2006.01)
*A61B 90/00* (2016.01)

(52) U.S. Cl.
CPC ..... *A61B 90/03* (2016.02); *A61B 2017/00778* (2013.01); *A61B 2017/00862* (2013.01); *A61B 2017/00969* (2013.01); *A61B 2017/1107* (2013.01); *A61B 2017/320064* (2013.01)

(58) Field of Classification Search
CPC ...... A61B 2017/00269; A61B 1/00064; A61B 1/00087; A61B 90/03; A61B 2017/32116; A61B 2017/320028; A61B 10/0233; A61B 10/025; A61B 10/0275; A61B 17/32053; A61B 17/3205; A61B 17/3209; A61B 177/3211; A61B 10/02; A01N 1/00; A01N 1/02
USPC .................. 606/170, 167; 600/564
See application file for complete search history.

(56) References Cited

U.S. PATENT DOCUMENTS

| | | | |
|---|---|---|---|
| 4,925,449 A * | 5/1990 | Saez .................. | A61M 5/007 222/386 |
| 5,092,873 A | 3/1992 | Simpson et al. | |
| 5,192,294 A * | 3/1993 | Blake, III ........ | A61B 17/32053 606/184 |
| 5,304,190 A * | 4/1994 | Reckelhoff .... | A61B 17/320016 30/134 |
| 5,395,313 A * | 3/1995 | Naves ................ | A61B 17/1608 600/564 |
| 5,445,638 A | 8/1995 | Rydell et al. | |
| 5,492,130 A | 2/1996 | Chiou | |
| 5,922,003 A * | 7/1999 | Anctil ............. | A61B 17/32002 156/293 |
| 6,488,693 B2 * | 12/2002 | Gannoe ......... | A61B 17/320016 604/164.12 |
| 8,388,550 B2 | 3/2013 | Koehler | |
| 8,696,686 B2 | 4/2014 | Drews et al. | |
| 2003/0074014 A1 * | 4/2003 | Castaneda ...... | A61B 17/320016 606/167 |
| 2004/0210245 A1 * | 10/2004 | Erickson ........... | A61B 17/3468 606/167 |
| 2005/0096694 A1 * | 5/2005 | Lee .................. | A61B 17/00234 606/205 |
| 2010/0298737 A1 * | 11/2010 | Koehler ............ | A61B 10/0275 600/567 |

\* cited by examiner

TRANSECTION DEVICE

This application claims the benefit of U.S. Provisional Application No. 62/073,337, filed on Oct. 31, 2014, the contents of which are incorporated herein by reference.

FIELD OF THE INVENTION

This present disclosure relates to a transection device. More particularly, the present disclosure relates to a transection device for tissue or vessels.

BACKGROUND OF THE INVENTION

In liver transplantation, there are two particularly challenging anastomoses: the hepatic artery and the bile duct. These structures are very delicate such that unnecessary and potentially excessive manipulation and handling may create tissue damage that may ultimately affect the functionality of the connections to the body. During the initial phase of operation (the hepatectomy phase) both structures must be ligated, only to be later transected again to create a smooth, regular, non-ischemic and defined surface for re-connection of these structures to those related structures of the donor organ. These "transections" are currently made in a rather imprecise and cumbersome fashion with scissors of various types, often leading to excessive handling and the creation of "stumps" that are often irregular and difficult to manage.

SUMMARY OF THE INVENTION

In at least one aspect of the present disclosure, the device described herein may be utilized to create the "cuffs" for the hepatic artery and bile stumps in a more precise manner which will facilitate management of these anastomoses while potentially saving time in performing the procedure and resulting in fewer complications related to these connections. While the specific use of the device described herein is the transaction of delicate tubular structures in the setting of liver (hepatic artery and bile duct), kidney (ureter) and any solid organ transplant, it is recognized that the device may be configured for a wide range of applications, for example, in vascular and other surgical settings other than those related to transplantation. Furthermore, the device is not limited to use on in vivo human tissue, but may be utilized in other applications, for example, in non-human animals and in vitro laboratory or other procedures. The device can be utilized in any setting in which a simplified way to create a uniform surface to lessen the complex nature of anastomoses is desirable.

At least one exemplary embodiment of the present disclosure provides a transection device including a hollow tubular body extending from a proximal end to a distal end. A plurality of stabilizing members extend from the distal end of the tubular body and define a reduced diameter opening into a receiving chamber adjacent the distal end of the tubular body. A blade is positioned within the tubular body and moveable between an initial position within the tubular body to an extended position wherein at least a portion of the blade extends into the receiving chamber. A depressible member extends from the proximal end and is configured to move the blade between the initial position and the extended position. A compression member may be positioned between a portion of the plunger member and the blade.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

Referring to FIGS. 1-5, an exemplary transection device 10 in accordance with an embodiment of the invention will be described. The transection device 10 includes a tubular body 20 extending from an open proximal end 21 to an open distal end 23 with a hollow chamber 22 defined therebetween. While the ends 21, 23 are illustrated as opened, it is recognized that either end may be closed or sealed other than the passage of the plunger or blade as described hereinafter. In the illustrated embodiment, the body 20 has a curved configuration with the axis of the proximal end 21 angled at approximately 45° relative to the axis of the distal end 23. The body 20 may have other configurations with more or less of an angle or alternatively may be a straight configuration.

A pair of finger rests 24 extend from the body 20 proximate the proximal end 21 thereof. The finger rests 24 allow the user to hold the device 10 in one hand, while still being able to access and actuate the plunger 34 as described hereinafter. While the finger rests 24 are illustrated as rings, they may have various other configurations.

Figure 1:
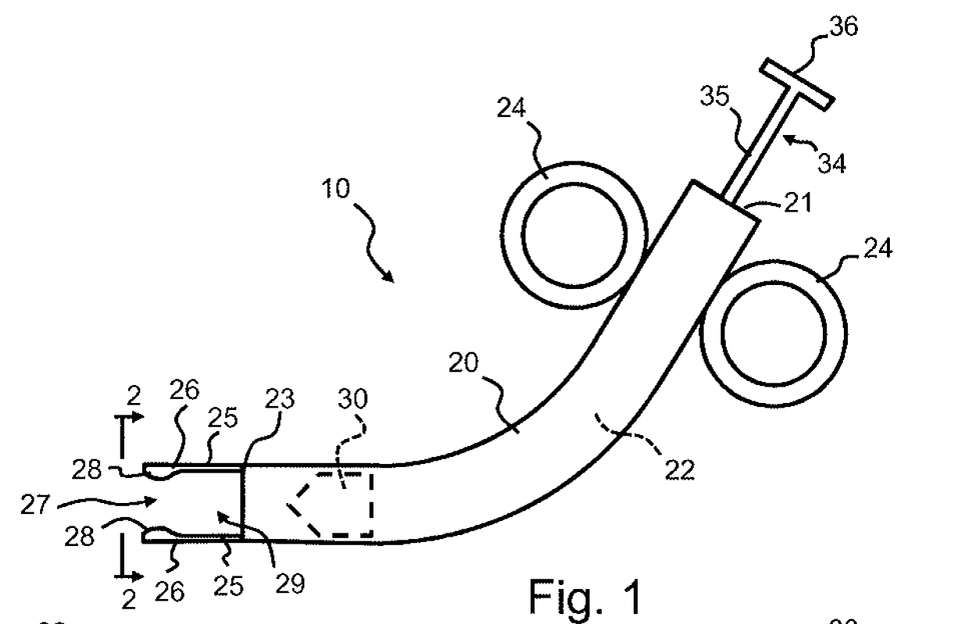
FIG. 1 is a side elevation view of an exemplary transection device in accordance with an embodiment of the present invention.
Figures 2, 3:
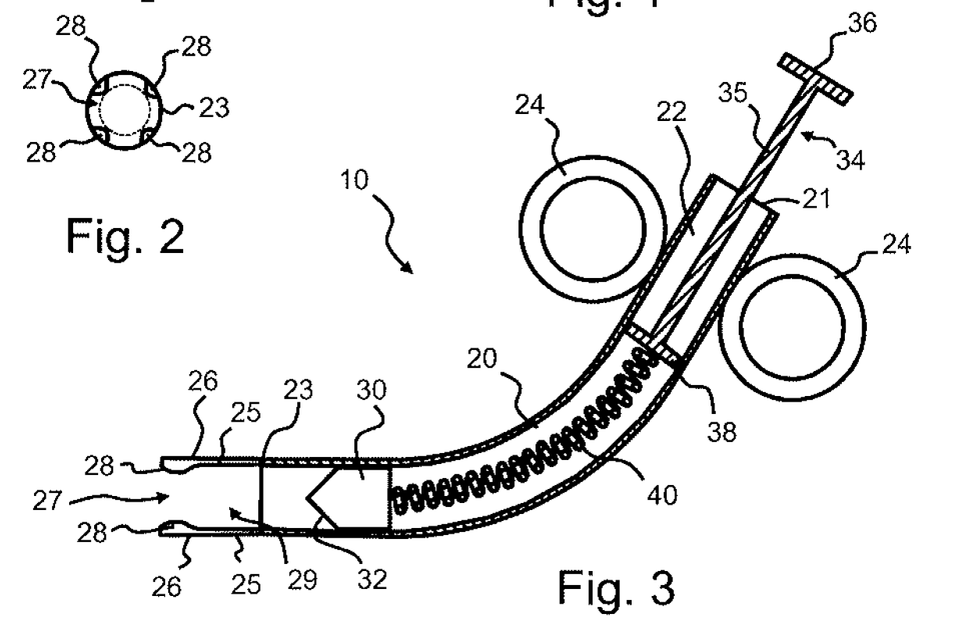
FIG. 2 is an elevation view of the distal end of the device as indicted by the arrows 2-2 in FIG. 1.
FIG. 3 is a cross-sectional view of the device of FIG. 1 in an initial position.
Figure 4:
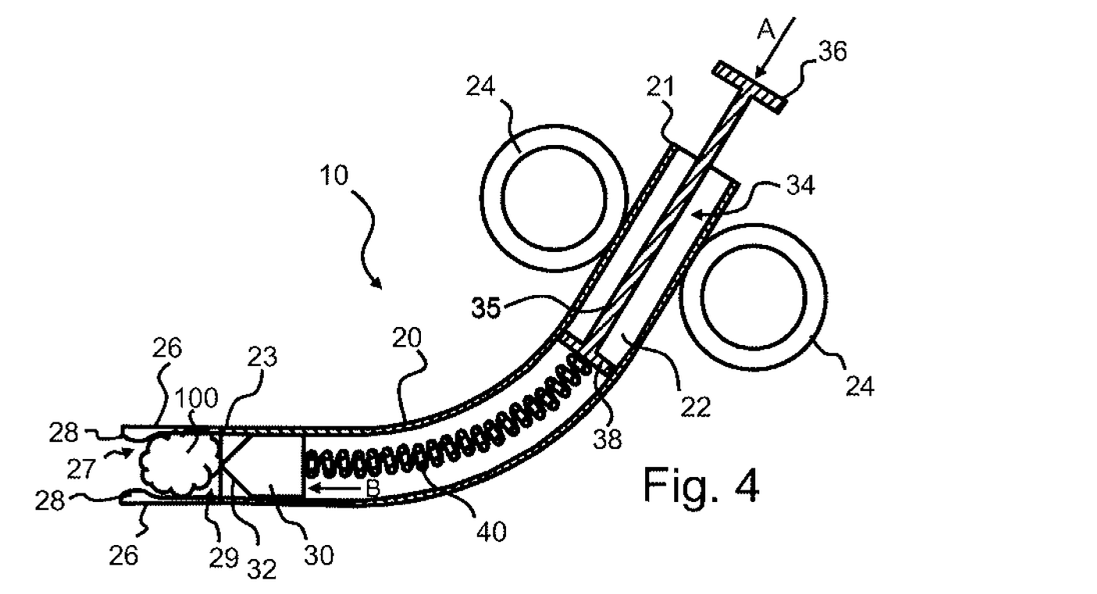
FIGS. 4 and 5 are cross-sectional views similar to FIG. 3 illustrating progressive actuation of the transection device.

A plurality of stabilizing members 26 extend distally of the distal end 23 of the body 20. Each stabilizing member 26 includes a flexible arm 25 extending from the body 20 with an inwardly extending protrusion 28 at the distal end thereof. As illustrated in FIGS. 1 and 2, the protrusions 28 extend toward one another to define a reduced diameter opening 27 and a retaining chamber 29 between stabilizing members 26.

While four stabilizing members 26 are illustrated, the device may have more or fewer. Additionally, the stabilizing members are not limited to the illustrated configuration, but may have other configurations and may contain additional features such as a synthetic coating or serrations. The reduced diameter opening 27 remains open in the distal direction such that the device 10 may be moved distally toward a target tissue or vessel 100, which will pass between the protrusions 28 and be retained within the chamber 29. The flexible nature of the arms 25 facilitates expansion of the opening 27 to allow passage of the tissue or vessel 100 therethrough, however, provides a sufficient holding force during the transection. The distal opening avoids the need for a portion of the device 10 to be extended past the tissue or vessel to align with an inward chamber.

The invention is not limited to a distal facing opening. In the embodiment illustrated in FIG. 7, the device 10" includes a tubular body 20' with a platform 17 extending from the distal end 23. The stabilizing members 26' extend from the platform 17, preferably perpendicular thereto, such that the opening 27' into the chamber 29 faces generally perpendicular to the axis of the distal end of the tubular body 20'. The stabilizing members 26' each include a flexible arm 25' with an inwardly extending protrusion 28' at the distal end thereof, similar to the previous embodiment. Other configurations may also be utilized.

Referring to FIG. 3, a cutting member 30 is positioned within the tubular body 20 proximate to the distal end 23. The illustrated cutting member 30 is a blade with a double-edge cutting surface 32 facing toward the distal end 23, however, it is not limited to such and may have other configurations, for example, a concave, serrated or multi-edged structure or blade. The blade 30 is configured for linear motion from the illustrated initial position to an extended position wherein the blade 30 extends into the retaining chamber 29 (see FIGS. 4 and 5 for progression of the blade toward the extended position).

Figure 5:
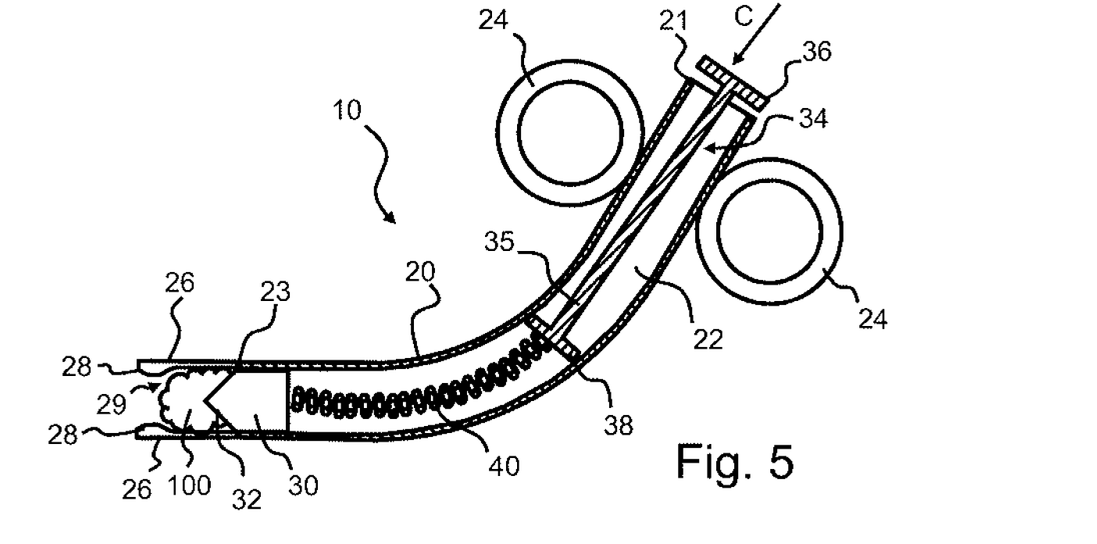

Motion of the blade 30 is controlled by a plunger 34 or similar depressible member extending from the proximal end 21. In the illustrated embodiment, the plunger 34 includes a shaft 35 extending between a contact surface 36 and a force applying surface 38. While it is possible for the force applying surface 38 to directly contact and push the blade 30, it is preferred that a compression member 40 extends between the force applying surface 38 and the blade 30. In the exemplary embodiment of FIGS. 1-5, the compression member 40 is in the form of a compressible spring. During initial depression of the plunger 34 as indicated by arrow A in FIG. 4, the compression member 40 will maintain its original configuration and simply move the blade 30 distally since there is no resistance on the blade 30. Once the blade 30 contacts the target tissue or vessel 100, as illustrated in FIG. 5, the compression member 40 is configured to compress to some degree such that the tissue or vessel 100 is not subject to the full force applied to the plunger 34, but instead begins the transection in a less traumatizing manner. After full depression of the plunger 34, the compression member 40 may decompress and further extend the blade 30 in a controlled manner. It is contemplated that the compression member is adjustable to adjust the respective forces.

Figure 6:
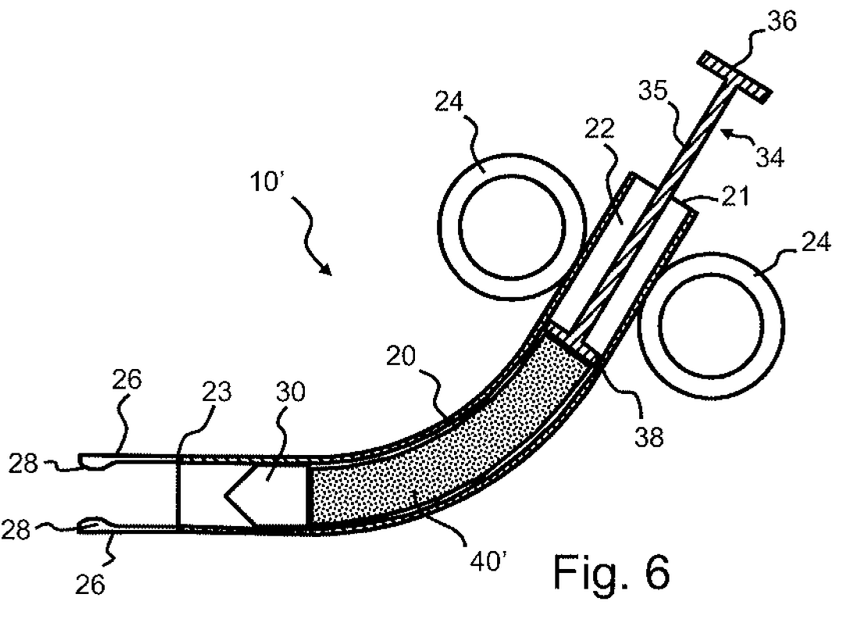
FIG. 6 is a cross-sectional view of another exemplary transection device in accordance with another embodiment of the invention.

Referring to FIG. 6, a transection device 10' in accordance with another exemplary embodiment of the invention is illustrated. The transection device 10' is the same as in the previous embodiment except that the compression member 40' is defined by a compressible mass. For example, the compressible mass may include a foam material, a rubber material or any other elastomeric material. Again, the compression member 40' is configured such that it will maintain its original configuration and simply move the blade 30 distally during initial depression of the plunger. Once the blade 30 contacts the target tissue or vessel 100, the compression member 40' is configured to compress to some degree such that the tissue or vessel 100 is not subject to the full force applied to the plunger 34, but instead begins the transection in a less traumatizing manner. After full depression of the plunger 34, the compression member 40' may decompress and further extend the blade 30 in a controlled manner.

Figure 7:
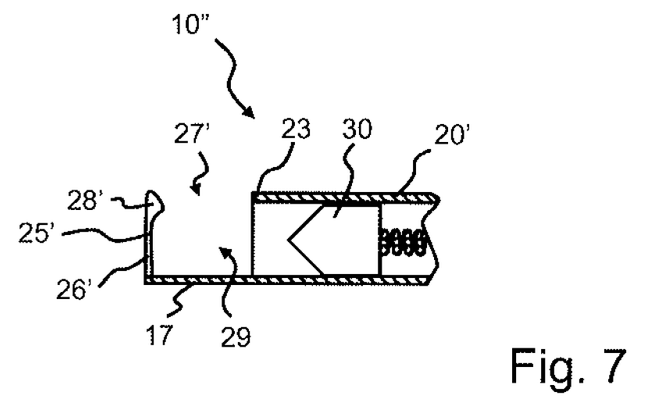
FIG. 7 is a cross-sectional view of a distal portion of another exemplary transection device in accordance with another embodiment of the invention.
Figure 8:
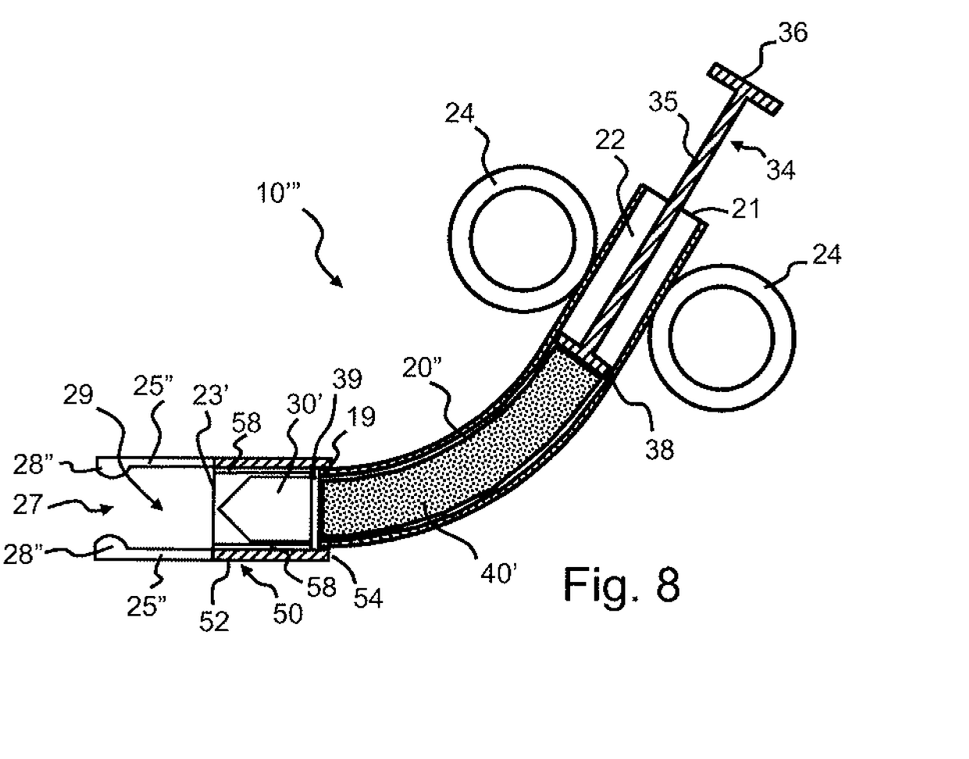
FIG. 8 is a cross-sectional view of another exemplary transection device in accordance with another embodiment of the invention.

Referring to FIGS. 7-8, a transection device 10''' in accordance with another exemplary embodiment of the invention is illustrated. The transection device 10''' is the same as in the previous embodiment except that the cutting member 30' is positioned within an interchangeable transection device head 50 which also defines the stabilizing members 26". The tubular body 20" has a truncated distal end 19 which ends proximate the distal end of the compression member 40'. The interchangeable head 50 includes a body 52 with an open end 54 configured to connect to the truncated distal end 19, for example, via threads 56. The opposite end of the body 52 defines the distal end 23' when the head 50 is connected to the tubular body 20" such that the tubular body 20" and the head 50 together define a tubular body extending from a proximal end 21 to a distal end 23'. The stabilizing members 26" extend from the body 52 with each stabilizing member 26" including a flexible arm 25" with an inwardly extending protrusion 28" at the distal end thereof, similar to the previous embodiments.

Figure 9:
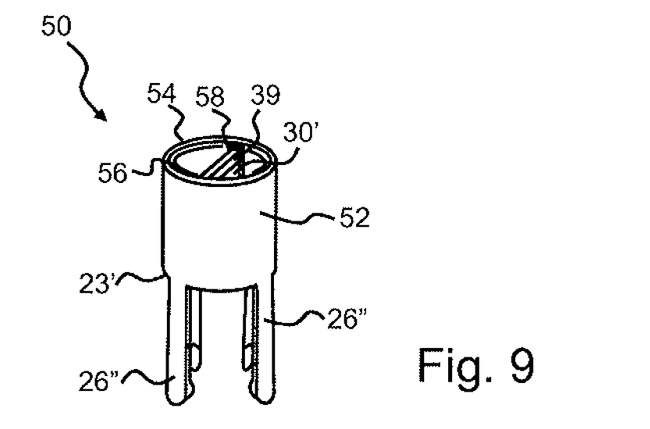
FIG. 9 is a perspective view of an exemplary interchangeable head of the transection device of FIG. 8.

The cutting member 30' is positioned within the body 52 and is configured for movement relative thereto such that the cutting member 30' is moveable between an initial position and an extended position similar to the previous embodiments. In the present embodiment, the cutting member 30' is connected to a guide block 39 which moves in opposed internal tracks 58 defined in the inside surface of the body 52. When the head 50 is connected to the tubular body 20' the guide block 39 is positioned adjacent the compression member 40' such that actuation of the plunger 34 will move the cutting member 30' in a manner similar to the previous embodiments. While the present embodiment is illustrated with the compression member 40', it is recognized that it may utilize the compression member 40 of the first embodiment or any other desired compression member or no compression member wherein the plunger 34 will directly contact the guide block 39.

The interchangeable head 50 allows the transection device 10' to be easily customized to a particular application. For example, different interchangeable heads 50 may be available with different configurations of stabilizing members 26" or with different cutting members 30'. The interchangeable head also allows the head 50 to be provided as a disposable part of the device. For example, the head 50 may be provided in a sterile package while the remainder of the device is sterilized and re-used. It is understood that other components of the device, for example, the plunger and compression member, or the entire device, may be disposable. As another alternative, the interchangeable heads 50 may be configured to be sterilized and re-used while other components are disposable.

Figure 10:
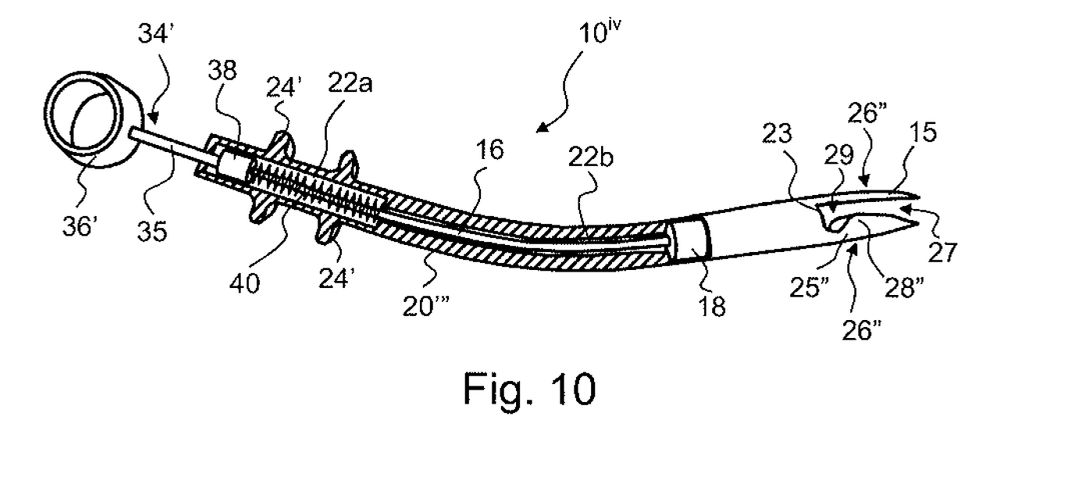
FIG. 10 is a perspective view, in partial cross-section, of another exemplary transection device in accordance with another embodiment of the invention.
Figure 11:
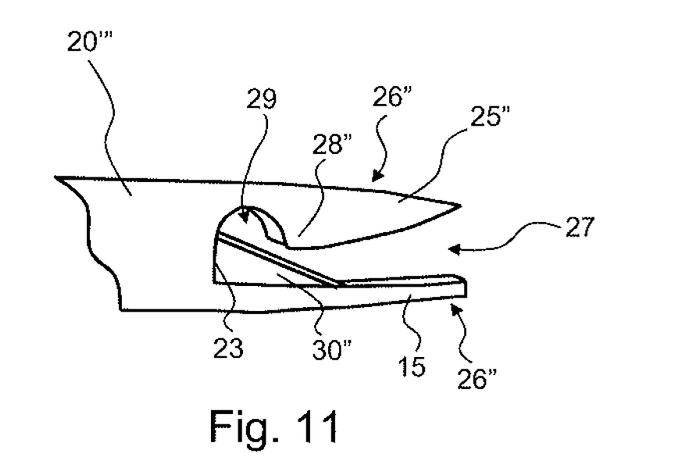
FIG. 11 is an expanded perspective view of a portion of the transection device of FIG. 10.

Referring to FIGS. 10 and 11, an exemplary transection device 10' in accordance with another embodiment of the invention will be described. The transection device 10' includes a tubular body 20' extending from an open proximal end to an open distal end 23. In the present embodiment, the finger rests 24' take the form of spaced apart radial discs extending about the tubular body 20' and the contact surface 36' of the plunger 34' is in the form of a ring. With this configuration, a user can position their thumb through the ring of the contact surface 36' and two fingers between the discs of the finger rests 24' to manipulate the device 10$^{iv}$.

With the tubular body 20''', the chamber includes a proximal portion 22a and a distal portion 22b, with the proximal portion 22a having a larger cross-section than the distal portion 22b such that a shoulder is defined therebetween. The shaft 35 and force applying surface 38 of the plunger assembly 34' or similar depressible member extend into the proximal portion 22a of the chamber, with an extension member 16 extending from the force applying surface 38, through the distal portion 22b of the chamber and into contact with a block 18 of the cutting assembly. The compression member 40 is positioned within the proximal portion 22a of the chamber about the extension member 16. The compression member 40 extends between the contact surface 38 and the block 18. With such a configuration, depression of the plunger 34' will push the extension member 16 and the block 18 to move the cutting member 30', however, such will be against the force of the compression member 40 with the resultant control as described above.

As in the previous embodiments, a plurality of stabilizing members 26'' extend distally of the distal end 23 of the body 20'''. In the present embodiment, two stabilizing members 26'' are provided. One of the stabilizing members 26'' includes a flexible arm 25'' extending from the body 20''' with an inwardly extending protrusion 28'' at the distal end thereof. The other stabilizing member 26'' includes a generally linear arm 15 without any protrusion. The reduced diameter opening 27 is defined between the protrusion 28'' and the arm 15 and the retaining chamber 29 is defined between the stabilizing members 26''. As illustrated in FIG. 11, the cutting member 30'' has a single cutting edge facing toward the linear arm 15 such that the linear arm 15 supports the target tissue as the cutting member 30'' moves thereacross. In other aspects, the transection device 10' functions in a manner similar to the previously described embodiments.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. A transection device comprising:
   a curved tubular body extending from a proximal end to a distal end, said curved tubular body having a wall and an internal chamber extending between the proximal and distal ends, wherein said curved tubular body has a receiving chamber proximate to the distal end, said receiving chamber defined by the distal end and an opening in the wall, said receiving chamber comprising at least one protrusion extending toward a center of said opening;
   a cutting member positioned within the curved tubular body and moveable between an initial position within the curved tubular body to an extended position within the receiving chamber wherein at least a portion of the cutting member extends into the receiving chamber; and
   a depressible member extending from the proximal end, and configured to move the cutting member between the initial position and the extended position, wherein the depressible member has a contact surface positioned outside of the curved tubular body, and a force applying surface within the curved tubular body; and
   a coil spring compressible in an axial direction of the curved tubular body, the coil spring extending from the cutting member to the force applying surface of the depressible member, the coil spring being configured to extend the cutting member toward the at least one protrusion in a controlled manner after being compressed,
   wherein the force applying surface directly contacts the coil spring which in turn directly contacts the cutting member.

2. The transection device according to claim 1 wherein an axis of the proximal end is angled relative to an axis of the distal end.

3. The transection device according to claim 2 wherein the axis of the proximal end is angled relative to the axis of the distal end by about 45°.

4. The transection device according to claim 1 wherein opposed finger rests extend outwardly from the tubular body proximate to the proximal end.

5. The transection device according to claim 1, wherein the depressible member is a plunger.

6. The transection device according to claim 1 wherein the cutting member has a double-edge cutting surface.

7. A transection device comprising:
   a curved tubular body extending from a proximal end to a distal end, said curved tubular body having a wall and an internal chamber extending between the proximal and distal ends, wherein said curved tubular body has a receiving chamber proximate to the distal end, said receiving chamber defined by the distal end and an opening in the wall, said receiving chamber comprising at least one protrusion extending toward a center of said opening;
   a cutting member positioned within the curved tubular body and moveable between an initial position within the curved tubular body to an extended position within the receiving chamber wherein at least a portion of the cutting member extends into the receiving chamber;
   a depressible member extending from the proximal end, the depressible member being configured to move the cutting member between the initial position and the extended position, wherein the depressible member has a contact surface positioned outside of the curved tubular body, and a force applying surface within the curved tubular body; and
   a compressible mass formed of an elastomeric material, the compressible mass being compressible in an axial direction of the curved tubular body and extending from the cutting member to the force applying surface of the depressible member, the compressible mass being configured to extend the cutting member toward the at least one protrusion in a controlled manner after being compressed,
   wherein the force applying surface directly contacts the compressible mass which in turn directly contacts the cutting member.

8. The transection device of claim 7, wherein the at least one protrusion is flexible, the at least one protrusion being configured to facilitate expansion of the opening such that a tissue may be passed into the receiving chamber and be retained in the receiving chamber during a transection.

9. A transection device comprising:

a curved tubular body extending from a proximal end to a distal end, said curved tubular body having a wall and an internal chamber extending between the proximal and distal ends, wherein said curved tubular body has a receiving chamber proximate to the distal end, said receiving chamber defined by the distal end and an opening in the wall, said receiving chamber comprising at least one flexible protrusion configured to facilitate expansion of the opening such that a tissue may be passed into the receiving chamber and be retained in the receiving chamber during a transection;

a cutting member positioned within the curved tubular body and moveable between an initial position within the curved tubular body to an extended position within the receiving chamber wherein at least a portion of the cutting member extends into the receiving chamber; and a depressible member extending from the proximal end, and configured to move the cutting member between the initial position and the extended position, wherein the depressible member has a contact surface positioned outside of the curved tubular body, and a force applying surface within the curved tubular body; and a coil spring compressible in an axial direction of the curved tubular body, the coil spring extending from the cutting member to the force applying surface of the depressible member, wherein the force applying surface directly contacts the coil spring which in turn directly contacts the cutting member.

10. The transection device of claim 9, wherein the coil spring is configured to extend the cutting member toward the at least one flexible protrusion in a controlled manner after being compressed.

11. The transection device of claim 9, wherein the coil spring is configured to urge the cutting member toward the at least one flexible protrusion during compression and move the blade away from the distal end after being compressed.

12. The transection device of claim 9, wherein the coil spring is configured to:

dampen a force applied by the cutting member to the tissue retained in the receiving chamber during the transection; and move the cutting member toward the at least one flexible protrusion after being compressed.

* * * * *